United States Patent [19]

Ilardi et al.

[11] Patent Number: 5,232,633
[45] Date of Patent: Aug. 3, 1993

[54] SULFOETHYL CARBONATE WETTING AGENTS AND THEIR USE IN DETERGENT COMPOSITIONS

[75] Inventors: Leonora M. Ilardi, Englewood; Stephen Madison, Valley Cottage; Deanne Oppermann, Ridgewood, all of N.J.

[73] Assignee: Lever Brothers, New York, N.Y.

[21] Appl. No.: 901,449

[22] Filed: Jun. 19, 1992

[51] Int. Cl.$^5$ .................... C11D 1/12; C07C 69/76; C07C 69/66
[52] U.S. Cl. ..................... 252/554; 252/549; 252/553; 252/557; 252/558; 252/530; 252/535; 252/555; 252/556; 252/536; 252/537; 252/539; 252/540; 560/60; 560/63; 560/186
[58] Field of Search ............... 252/549, 552, 553, 554, 252/558, 557, 533, 534, 535, 538, 539, 555, 530, 556; 560/60, 63, 186

[56] References Cited

U.S. PATENT DOCUMENTS

| | | | |
|---|---|---|---|
| 1,881,172 | 10/1932 | Daimler et al. | 252/354 |
| 1,916,776 | 7/1933 | Steindorff et al. | 252/354 |
| 3,393,213 | 7/1968 | Kiefer et al. | 252/557 |
| 3,880,897 | 4/1975 | Landy | 554/92 |
| 4,745,162 | 5/1988 | Harris | 252/351 |
| 4,766,153 | 8/1988 | Casciani | 560/186 |
| 4,954,282 | 9/1990 | Rys et al. | 252/557 |

FOREIGN PATENT DOCUMENTS

| | | |
|---|---|---|
| 0353503 | 2/1990 | European Pat. Off. |
| 60-186599 | 9/1985 | Japan . |
| 2-232298 | 9/1990 | Japan . |

*Primary Examiner*—Paul Lieberman
*Assistant Examiner*—Bradley A. Swope
*Attorney, Agent, or Firm*—James J. Farrell

[57] ABSTRACT

Carbonated isethionate surfactants, compositions containing them and methods for their preparation are disclosed.

13 Claims, No Drawings

SULFOETHYL CARBONATE WETTING AGENTS AND THEIR USE IN DETERGENT COMPOSITIONS

BACKGROUND OF THE INVENTION

1. Field of the Invention

The present invention relates to sulfoethyl carbonate-type wetting agents as well as to compositions comprising these carbonates.

2. Related Art

The use of sulfoethyl derivatives of fatty acids is well known in the art, see, for example, U.S. Pat. Nos. 1,881,172; 1,916,776; 3,393,213 and 4,954,282.

Derivatives of this material while having good lathering characteristics and being mild surfactants are nevertheless somewhat hydrolytically unstable. One derivative of this material is a very mild surfactant which is employed in commercial personal washing bars and may also be used in other compositions employing surfactants. The coco derivative of these sulfoethyl compounds, known as sodium cocoyl isethionate or sodium 2-sulfoethyl cocoate is used extensively in personal washing bars. It is believed that one of the reasons for mildness is due to the compounds susceptibility to cleavage by skin esterase enzymes. The cleavage by-products coco fatty acid and sodium isethionate are known to be milder to skin than the active itself. It is theorized that these surfactants could be made even milder by preparing a derivative which, after cleavage, is even more innocuous than, for example, coco fatty acid.

In 1984, Shin Nippon Rika Co., Ltd. in Japanese Patent Application 59-42347 disclosed a detergent composition with one surfactant of the general formula: $RO[(C(O)OCH_2CH_2O)_m(CH_2Ch_2O)_n]CH_2CH_2SO_3X$ where R is an alkyl group, hydroxyalkyl group containing an ether group, with a carbon number of 2-20; X is Li, Na, $NH_4+$, or an amine residue; and $m+n=2-20$. In 1990, Henkel Corp. in European Patent 0,353,503 disclosed a carbonate based surfactant. The structure of the Henkel patent was not based on isethionate.

The compounds developed in the art are not, completely satisfactory.

Accordingly, it is an object of the present invention to provide improved surfactant derivatives which have good lathering capabilities, provide a good critical micelle concentration (CMC), are less sensitive to calcium ion concentration and have good hydrolytic stability.

A further object is to overcome one or more disadvantages of the art.

Other objects of the present invention will become apparent through the following summary, detailed discussion and examples.

SUMMARY OF THE INVENTION

The present invention is a new surfactant. The surfactant is the carbonate analogue of fatty acid ethane sulfonic acid esters. This is a fatty alcohol sulfoethyl carbonate.

As mentioned above, compounds of the present invention are also susceptible to cleavage by skin enzymes but the cleavage by-products are now sodium isethionate and a fatty alcohol. Fatty alcohols are essentially non ionizable and in some cases may be milder than fatty acids. These compounds may be used in personal washing or household products as cleaning agents that are relatively mild to the skin without sacrificing hydrolytic stability, good CMC and good lathering together with relative ease of preparation.

More specifically, applicants have found that such sulfoethyl fatty alcohol carbonates are relatively hydrolytically stable. In addition, the carbonates perform as well as or better than the fatty acid esters of non-carbonated isethionates with lather volume and have a lower CMC.

The present invention relates to a compound of the formula:

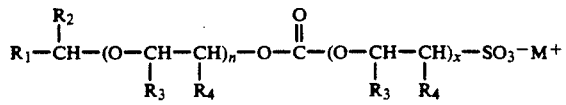

wherein n is a number from 0 to 10;

wherein x is 1 or 2;

wherein $R_1$ through $R_6$ inclusive may be independently hydrogen, aryl, cycloalkyl, alkylaryl, alkylene or straight or branched $C_{1-18}$ alkyl and;

wherein $M^+$ is alkali metal, alkaline earth metal, ammonium or alkylammonium.

These surfactant compounds may be used in household or personal cleaning products employing surfactants. In some respects, they have been found to be equivalent to or superior to the ester compounds of the prior art.

As indicated in more detail below, the surfactant compounds of the invention may be prepared by reacting selected alcohols and alkoxyalcohol with phosgene followed by reaction with sodium isethionate. Since these alkoxyalcohols are typically formed by the reaction of a mixture of alkylene oxide groups, the resulting alkoxyalcohol generally contains a mixture of alkoxylated groups (e.g., the molecule might contain both ethoxy and propoxy groups). Stated differently, if $n>1$ (i.e., 2-4), the group may differ from one alkoxylate group to another.

Further, since the alkoxyalcohol or alcohol chloroformate obtained is then reacted with isethionate which may comprise a mixture of R groups, the ethoxylated isethionate carbonate produced may comprise a mixture of $R_3$, $R_4$, $R_5$ and $R_6$ groups as well ranging up to about $C_4$.

The invention in a second embodiment relates to the use of the novel surfactant compounds and compositions containing these compounds. The compositions in which the surfactant may be used include both heavy and light-duty liquid detergent compositions, detergent bar compositions and personal product compositions (e.g., shampoos or facial cleaners or indeed anything containing surfactants).

For the reasons noted above, the compounds used in the compositions of this aspect of the invention may be mixtures of alkoxylated or unalkoxylated carbonate isethionates wherein each carbonate might contain a mixture of alkoxylated groups and wherein there is typically a mixture of alkyl chain lengths among the various alcohols and isethionates.

DETAILED DESCRIPTION OF THE INVENTION

The present invention provides novel carbonate based isethionate surfactants having the formula:

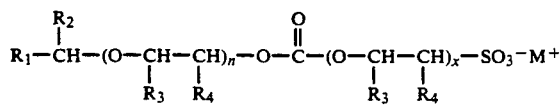

wherein n is a number from 0 to 10;

wherein x is 1 or 2;

wherein $R_1$ through $R_6$ inclusive may be independently hydrogen, aryl, cycloalkyl, alkylaryl, alkylene or straight or branched $C_{1-18}$ alkyl; and wherein $M^+$ is alkali metal, alkaline earth metal, ammonium or alkylammonium.

When these carbonate based surfactant molecules are compared to esters analogues, significant improvements in selected performance parameters and calcium tolerance are observed.

Preparation

(A) Preparation of Sodium Sulfoalkyl Alkyl Carbonates

The carbonate surfactants were prepared in two steps which are outlined below in Process I:

The first step is the preparation of the alkyl chloroformate. The second step is the condensation of the alkyl chloroformate with the appropriate isethionate. The branched isethionates were prepared from the appropriate 1,2-epoxyalkane and sodium metabisulfite in water. The resulting solids were recrystallized from ethanol and water and dried thoroughly before use.

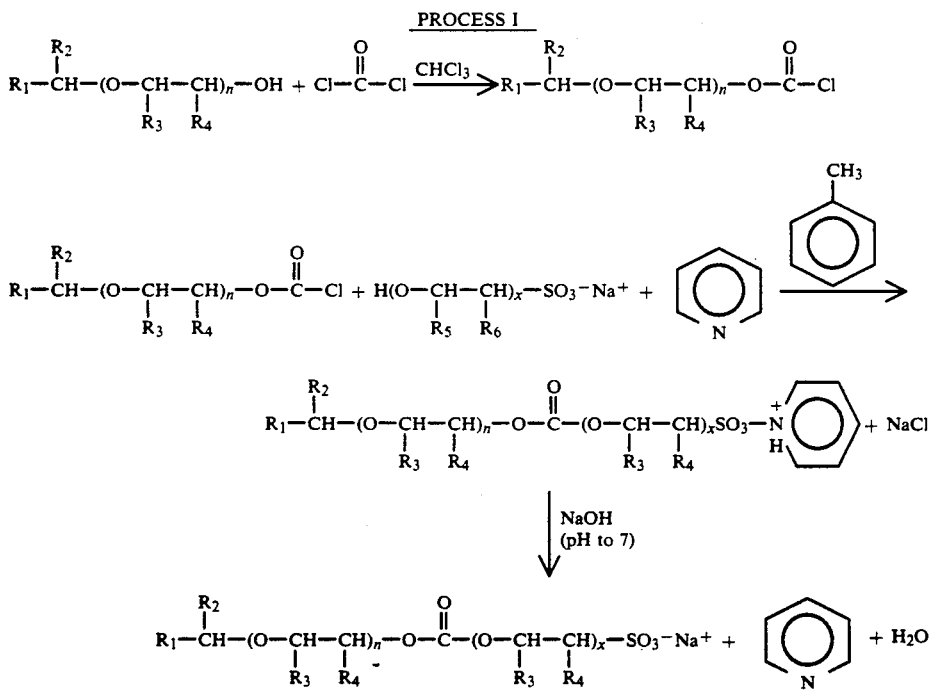

As indicated in Process I above, since the starting alcohol if alkoxylated is formed from a mixture of alkylene oxides, the resulting alcohol chloroformate if alkoxylated may comprise a mixture of alkoxy groups (e.g., both ethoxy and propoxy groups). As also indicated above, the starting fatty alcohol is generally a mixture of varying chain lengths $R_1$ and $R_2$. The reaction product will accordingly generally be a mixture of alkoxylated carbonated isethionates with a distribution of various $R_1$ and $R_2$ alkyl groups.

Compositions

The alkoxylated isethionate carbonate surfactant compounds of the invention may be used in various personal washing compositions such as toilet bars or facial cleansers as well as other compositions where mild surfactants might be desired (e.g., light duty liquid dishwashing compositions).

These examples are not intended to be exhaustive of the compositions in which such mild surfactants might be used and other compositions in which such mildness might be desirable would be apparent to those skilled in the art.

In general, the compositions comprise 2-85% of a surfactant selected from the group consisting of anionic, nonionic, cationic, ampholytic and zwitterionic surfactants or mixtures thereof and the compound or a mixture of the compounds of the invention.

Examples of the many surfactants which may be used are set forth in surface active agents and detergents by Schwartz et al., Interscience Publishers, hereby incorporated by reference into the present specification.

The present invention is further illustrated by the following examples which are not intended to be limiting in any way.

EXAMPLE 1

Preparation of Alkyl Chloroformates

N-Dodecyl Chloroformate: Into a 500 mL three-necked round-bottomed flask equipped with a magnetic stirrer and maintained at $-20°$ C. was condensed 43.3 g (0.438 moles of phosgene) typically an excess of phosgene is used. After this transfer is complete, approximately 150 mL of ethanol-free, dry chloroform is added to the flask. To this mixture is added freshly distilled 1-dodecanol (41.3 g., 0.222 moles) dropwise using an addition funnel. During the addition, the reaction vessel is kept chilled to $-20°$ C.; upon completion of the addition, the reaction vessel is allowed to warm to room indicates the disappearance of the OH stretch at 3200–3400 cm$^{-1}$ and the appearance of the sharp peak at 1780 cm$^{-1}$ indicative of the chloroformate. The chloroform, HCl and excess phosgene are removed by placing the reaction mixture under vacuum first using a diaphragm pump and then with high vacuum. To ensure all impurities are removed, the liquid chloroformate is distilled under reduced pressure (boiling point: 90° C. at 0.1 mm Hg). The product is made in 99% yield (54.6 g, 0.220 moles) and is a clear, colorless liquid. $^1$H NMR (60 MHz, neat) δ 4.2 (2H, t), δ 1.5–1.8 (20H, m), δ 0.89 (3H, t). IR (neat) 1780 cm$^{-1}$ (carbonyl).

2-Dodecyl Chloroformate: The procedure is the same as for preparing n-dodecyl chloroformate except freshly distilled 2-dodecanol (41.3 g, 0.222 moles) is added to the phosgene mixture. 99% yields of 2-dodecyl chloroformate are obtained. The product is purified via distillation (90° C. at 0.1 mm Hg). $^1$H MNR (60 MHz, neat) δ 4.6–4.98 (1H,m), δ 1.5–1.8 (21H,m), δ0.89 (3H, t). IR (neat) 1780 cm$^{-1}$ (carbonyl).

C16 Guerbet Chloroformate: The procedure is the same as for preparing n-dodecyl chloroformate except C16 Guerbet alcohol obtained from Exxal Corp. is used and three equivalents of phosgene are used for every mole of alcohol. Yields of 98–99% are obtained for the desired chloroformate. The product is purified via distillation (100° C., 0.1 mm Hg). $^1$H NMR (60 MHz, neat) δ 3.8–4.2 (2H,m), δ 0.5–2.0 (31H,m). IR (neat) 1780 cm$^{-1}$ (carbonyl)

C18 Guerbet Chloroformate: The procedure is the same as for preparing C16 Guerbet chloroformate except C18 Guerbet alcohol from Exxal Corp. is used. The desired chloroformate is prepared in 98–99% yields. The product is purified by distillation (108° C., 0.1 mm Hg). $^1$H NMR (60 MHz, neat) δ 3.95–4.3 (2H,m), δ 0.5–2.0 (35H,m). IR (neat) 1780 cm$^{-1}$ (carbonyl).

Dodecyl (2EO) chloroformate: The procedure is the same as for preparing dodecyl chloroformate except dodecyl (2EO) alcohol (Novel II 12-32; ex Vista) is added to the phosgene mixture (20.0 g, 0.067 moles). The product is a clear colorless liquid; a yield of 25.0 g (100%) was realized. Because the material contains a distribution of ethylene oxide units, it was used without further purification. $^1$H NMR (60 MHz, neat) δ4.6–4.0 (12H, m), δ3.9–3.1 (~8H, m), δ2.0–0.6 (~23H, m), IR (nujol) 1780 cm$^1$ (carbonyl).

Dodecyl (4EO) chloroformate: The procedure is the same as for preparing dodecyl (2EO) chloroformate except Vista's Dodecyl (4EO) alcohol; Novel II 12-50 (41.5 g, 0.121 moles) is added to the phosgene mixture. The product is worked up in the same way; a yield of 99% (48.6 g, 0.120 moles) is realized. $^1$H NMR (60 MH, neat) δ4.9–4.5 (2H, m), δ4.2–3.2(~15H, m), δ2.2–0.9 (~23H, m), (IR (nujol) 1780 cm$^{-1}$ (carbonyl).

Dodecyl/tetradecyl (2EO) chloroformate: The procedure is the same as for preparing dodecyl (2EO) chloroformate except Vista's alcohol, Novel II 1214-30, a blend of ~75% ethoxylated dodecanol and ~25% ethoxylated tetradecanol, is added to the phosgene mixture. A yield of 53.7g (0.145 moles, ~100%) of product is obtained. $^1$H NMR (60 MHz, neat) δ4.5–4.0 (2H, m), δ4.5–3.1 (~8H, m), δ2.0–0.6 (~23H, m). IR (nujol) 1780 cm$^{-1}$ (carbonyl).

Preparation of Carbonates

Sodium 2-sulfoethyl dodecyl carbonate (SEDC): To a 500 mL three-necked round-bottomed flask equipped with a magnetic stirrer, oil bath with a temperature controlled hot plate stirrer, reflux condenser and calcium sulfate drying tube is placed 10.6 g (0.0716 moles) of sodium isethionate and 200 mL of dry toluene; to this is added 11.33 g (0.1432 moles) pyridine (ex Fisher) and 17.82 g (0.0716 moles) dodecyl chloroformate. All materials are in solution except for the isethionate. The reaction mixture is brought to reflux for 1.5 hours; a white precipitate is present in the reaction vessel. This solid is filtered off and analyzed to be sodium chloride as indicated by silver nitrate titration and as indicated by the absence of peaks in the NMR. The filtrate is stripped to obtain a white solid; $^1$H NMR identifies this material as the pyridinium salt of suloethyl dodecyl carbonate. The solid is triturated with 250 mL of diethyl ether and chilled overnight. The solid is then filtered and dissolved in water; its pH is 3.5 (indicative of the pyridinium salt). The pH is raised to 7 with dilute sodium hydroxide thus releasing an equivalent of pyridine. This mixture is placed under reduced pressure to remove the pyridine after which time it is freeze dried to remove the water. The resulting solid is purified by washing in 200 mL acetone followed by recrystallization from ethanol/water (200 mL/120 mL). The white crystalline solid is analyzed by 99+% active via hyamine titration. The yield of purified material is 86% (22.2 g., 0.0616 moles). $^1$H NMR (200 MHz,D$_2$O,TMS) δ 4.48 (2H,t), δ 4.15 (2H, t), δ 3.29 (2H,t), δ 1.1–1.7 (20H,m), δ 0.89 (3H,t). IR (nujol) 1741.7 cm$^{-1}$ (carbonyl).

Sodium 2-sulfoethyl 2-dodecylcarbonate (SE2DC): The apparatus is set up as in the preparation of sodium 2-sulfoethyl dodecyl carbonate. Sodium isethionate (17.2 g., 0.116 moles) is mixed with distilled 2-dodecyl chloroformate (29.3 g, 0.118 moles) and pyridine (28.0, 0.354 moles) in 200 mL of dry toluene. The mixture is stirred and refluxed for three hours after which time a white precipitate is seen. Analysis of the solid indicates that no sodium isethionate is present and it is identified as sodium chloride. The reaction mixture is decanted from this solid and is stripped of its toluene producing a light green colored semi-solid. This material is dissolved in 250 mL of diethyl ether and chilled overnight; a white precipitate results. This solid is filtered and dissolved in water; its pH is raised to 7 with dilute sodium hydroxide. The pyridine which is released is removed under vacuum and the resulting solution is freeze-dried. The white solid produced is washed with 400 mL of acetonitrile, 300 mL of acetone and recrystallized from ethanol/water (170 mL/100 mL). A white crystalline solid is obtained; it is analyzed as 99+% active via hyamine titration. The reaction yield is 57% (23.7 g, 0.0657 moles). $^1$H NMR (200 MHz,D$_2$O,TMS) δ 4.72–4.85 (1H,m), δ 4.32–4.65 (2H,m), δ 3.15–3.40 (2H,t), δ 0.65–1.75 (24H,m). IR (nujol), 1744.6 cm$^{-1}$ (carbonyl).

Sodium 2-sulfoisopropyl dodecyl carbonate (SIDC): The apparatus is set up as in the preparation of sodium 2-sulfoethyl dodecyl carbonate. Sodium 2-hydroxypropyl sulfonate (4) (22.4 g, 0.138 moles), dodecyl chloroformates (34.3 g, 0.138 moles), and pyridine 33.3 g, 0.421 moles) are mixed in 200 mL of toluene and are heated to reflux for 3 hours; NMR analysis of the toluene insoluble material shows no starting branched isethionate is present. The reaction mixture is decanted from the insoluble material and filtered; the filtrate is stripped of toluene producing a green-colored semi-solid. This material in turn is dissolved in diethyl ether and chilled overnight producing a white precipitate which is filtered, dissolved in water and treated with dilute aqueous sodium hydroxide until the pH=7. The pyridine which is produced is removed under vacuum and the resulting aqueous solution is freeze-dried producing the product. It is then washed with 450 mL of acetonitrile and recrystallized at 10° C. from ethanol/water (134 mL/66 mL). The product is analyzed as 95% active via hyamine titration with the balance being water as noted by NMR. The reaction yield is 58% (30.4 g, 0.813 moles). $^1$H NMR (200 MHz,$D_2O$,TMS) $\delta$ 5.10–5.28 (1H, m), $\delta$ 3.95–4.26 (2H,m), $\delta$2.95–3.38 (2H,m), $\delta$ 0.30–1.85 (26H,m). IR (nujol) 1743 cm$^{-1}$ (carbonyl).

Sodium 2-sulfoisopropyl 2-dodecyl carbonate (SI2DC): The apparatus is set up as in the preparation of sodium 2-sulfoethyl dodecyl carbonate. Sodium 2-hydroxypropylsulfonate (13.0 g, 0.0802 moles), 2-dodecyl chloroformate (20.0 g, 0.0804 moles) and pyridine (19.0 g, 0.240 moles) are mixed in 200 mL of toluene and are heated to reflux for 24 hours after which time the toluene insolubles are filtered off and the filtrate is stripped down to a green colored semi-solid. Approximately 250 mL of diethyl ether is used to dissolve the material and the solution is chilled overnight producing a white precipitate. This solid is filtered under nitrogen (due to its hydroscopic nature), washed with 400 mL of acetonitrile and acetone. The material is analyzed as 99% active via hyamine titration. The reaction yield is 20% (6.03 g, 0.0161 moles). $^1$H NMR (200 MHz, $D_2O$, TMS) $\delta$ 5.10–5.32 (1H,m), $\delta$ 4.20–4.89 (1H,m), $\delta$ 3.00–3.36 (2H,m), $\delta$ 0.62–1.90 (27H,m). IR (nujol 1741.8 cm$^{-1}$ (carbonyl).

Sodium 2-(1-sulfo)butyl dodecyl carbonate (S2DBC): The apparatus is set up as in the preparation of sodium 2-sulfoethyl dodecyl carbonate except a 1000 mL flask is used. Sodium 2-hydroxybutylsulfonate (40.0 g, 0.227 moles), n-dodecyl chloroformate (56.5 g, 0.227 moles), and pyridine (41.9 g, 0.454 moles) are mixed with 400 mL toluene and are heated to reflux for two hours after which time the clear toluene layer is decanted from the white emulsion/precipitate layer that lies on the bottom of the flask. This bottom layer is filtered of any salts and it is worked separately. Both layers are stripped of solvent, producing semi-solids; each is dissolved in cold diethyl ether and chilled overnight. The precipitates which form are filtered, placed in water and treated with dilute aqueous sodium hydroxide until the pH = 7. These solutions are freeze-dried; the resulting solids are washed with 500 mL acetonitrile and 400 mL acetone and recrystallized from ethanol/water (437 mL/281 mL for the solid resulting from the toluene layer; 44 mL/205 mL for the solid resulting from the white bottom layer). The second recrystallization for each solid used similar ratios. Analysis of the material via hyamine titration shows 99+% activity. The total reaction yield is 65% (576.33 g, 0.146 moles). $^1$H NMR (200 MHz,DMSO,TMS) $\delta$4.82–4.98 (1H,m), $\delta$ 3.95–4.10 (2H, broad t), $\delta$ 2.6–2.85 (2H,m), $\delta$ 1.0–2.0 (25H,m), $\delta$ 0.7–1.0 (3H,m). IR (nujol) 1742.136 cm$^{-1}$ (carbonyl).

Sodium 2-sulfoethyl C16 Guerbet carbonate (SEC16GC): The apparatus is set up as in the preparation of sodium 2-sulfoethyl dodecyl carbonate. Sodium isethionates (8.66 g, 0.589 moles), C16 Guerbet chloroformated (18.9 g, 0.062 moles), and pyridine (14.0 g, 0.177 moles) are mixed in 200 mL toluene. The reaction is stirred and heated to reflux for 1.5 hours after which time the toluene insolubles are filtered off. The filtrate is stripped down to a viscous semi-solid, dissolved in water and treated with dilute aqueous sodium hydroxide until the pH = 7. The sample is placed under reduced pressure to remove pyridine and the resulting solution is freeze-dried. The solid produced is dried and analyzed as 84.4% active via hyamine titration. The total reaction yield is 72%. $^1$H NMR (200 MHz,DMSO,TMS) $\delta$ 4.26 (2H,t), $\delta$ 3.98 (2H, broad s), $\delta$ 2.82 (2H,t), $\delta$ 0.6–1.8 ( 30H,m). FAB MS analysis shows that our surfactant as well as the starting Guerbet alcohol is a mixture of different alkyl chain lengths. IR (nujol 1745.55 cm$^{-1}$ (carbonyl).

Sodium 2-sulfoethyl C18 Guerbet carbonate (SEC18GC): The apparatus is set up as in the preparation of sodium sulfoethyl dodecyl carbonate. Sodium isethionate (10.6 g, 0.0714 moles), C18 Guerbet chloroformate (24.9 g, 0.0748 moles), and pyridine (17.0 g, 0.214 moles) are mixed in 200 ml of toluene and are heated to reflux for 1.5 hours after which time the toluene insolubles are filtered off and the filtrate is stripped down producing a viscous semi-solid. This solid is dissolved in water and is treated with dilute aqueous sodium hydroxide until the pH=7. The mixture is placed under reduced pressure to remove the liberated pyridine and is then freeze-dried. The resulting solid is analyzed as 92% active via hyamine titration. Total yield is 70%. (23 g, 0.0523 moles). $^1$H NMR (200 MHz,DMSO,TMS) $\delta$ 4.26 (2H,t), $\delta$ 3.98 (2H, broad s), $\delta$ 2.8 (2H,t), $\delta$ 0.5–1.8 ( 34H,m). FAB MS analysis shows that the surfactant is a mixture of different chain lengths due to the starting Guerbet alcohol. IR (nujol 1746 cm$^{-1}$ (carbonyl).

Sodium 2-sulfoethyl dodecyl (2EO) carbonate SED (2EO)C: To a 100 mL three-necked round-bottomed flask equipped with a magnetic stirrer, oil bath with a temperature controlled hot plate stirrer, reflux condenser and calcium sulfate drying tube is placed 6.8 g (0.046 moles) of sodium isethionate (ex Aldrich) and 75 mL of dry toluene; to this is added 7.2g (0.092 moles) pyridine (ex Fisher) and 15.0 g (0.0415 moles) dodecyl (2EO) chloroformate. All materials are in solution except for the isethionate. The reaction mixture is brought to reflux for 1.0 hour; a white precipitate is present in the vessel throughout the entire reaction. The reaction is monitored by the disappearance of sodium isethionate in the white precipitate. When no trace of organics is noted, the solid is filtered off and analyzed via silver nitrate titration to be sodium chloride. The resulting filtrate is placed under reduced pressure to remove the toluene and an off-white semi solid remains. NMR of this material identified it as the pyridinium salt of 2-sulfoethyl dodecyl (2EO) carbonate. The material is dissolved in water and its pH is raised to 7.0 with dilute sodium hydroxide thus releasing an equivalent of pyridine. This mixture is again placed under reduced pressure to remove the liberated pyridine and the resulting aqueous solution is freeze dried to remove the water. The resulting solid is washed with 200 mL of acetonitrile and then with 200 mL of acetone. The product is a white solid and is analyzed to be 77% active via hyamine titration and 4.43% sodium isethionate via HPLC. The total reaction yield is 49%. $^1$H NMR (300 MHz, $D_2O$, TMS) $\delta$4.4–4.6 (2H, m), $\delta$4.3 (2H, m), $\delta$4.13 (2H, m), $\delta$3.87–3.53 (~4H, m), $\delta$3.4–3.5 (2H, m), $\delta$3.2–3.3 (2H, m), $\delta$0.5–1.7 (23H, m). Triplets at $\delta$3.14 and $\delta$3.93 are from residual sodium isethionate. Broad singlet at $\delta$4.74 is from residual water. IR (nujol): 1741.81 cm$^{-1}$ (carbonyl).

Sodium 2-sulfoethyl dodecyl (4EO) carbonate: SED (4EO)C. The apparatus is set up as in the preparation of sodium 2-sulfoethyl dodecyl (2EO) carbonate except a 250 ml three-necked round bottom flask was used. Dodecyl (4EO) chloroformate (25 g, 0.0616 moles), sodium isethionate (8.43 g, 0.0569 moles), and pyridine (9.0 g, 0.11 moles) are combined in 150 mL of toluene. The reaction mixture is heated to refulx for 1 hour. NMR of the insoluble material indicates the absence of organic material. Fifteen mL of petroleum ether solvent is added to the mixture to facilitate the precipitation of the sodium chloride by product. The salt is filtered off from the mixture and the filtrate is placed under reduced pressure to remove the solvents. The resulting semi-solid is washed with ether; this material is then dissolved in water and its pH is adjusted to 7.0. After removal of the pyridine, the aqueous solution is freeze dried. The resulting material is a white solid and is analyzed to be 77% active via hyamine titration and 11.57% sodium isethionate via HPLC. The yield of recovered product is 30% (8.84 g, 0.0171 moles). $^1$H NMR (300 MHz, D$_2$O, TMS), $\delta$4.4–4.6 (2H, broad s), $\delta$4.2–4.4 (2H, broad s), $\delta$3.5–3.8 (~14H, m), $\delta$3.4 (2H, m), $\delta$3.2–3.3 (2H, m), $\delta$0.7–1.7 (23H, m). Multiplets at $\delta$3.1 and 3.9 are from residual sodium isethionate. Multiplet at $\delta$4.69 is from residual water; IR (nujol): 1738.97 cm$^{-1}$ (carbonyl).

Sodium 2-sulfoethyl tetradecyl/dodecyl (2EO) carbonate: SET/D (2EO)C. The apparatus is set up as in the preparation of sodium 2-sulfoethyl dodecyl (2EO) carbonate. Sodium isethionate (9.6 g, 0.065 mole) is combined with 150 mL of dry toluene, pyridine (10.2 g, 0.130 mole), and tetradecyl/dodecyl chloroformate (25.2 g, 0.0678 mole). The reaction mixture is stirred and heated to reflux for 3 hours. A white precipitate is present throughout the reaction. After this time the precipitate is filtered off and analyzed to be NaCl. The filtrate is placed under reduced pressure to remove the toluene and an off-white semi-solid results. This material is solubilized in diethyl ether and is allowed to cool in a refrigerator overnight. A white precipitate forms which is filtered off and subsequently dissolved in water; the pH of this solution is raised to 7.0 with dilute sodium hydroxide solution. The mixture is placed under reduced pressure to remove the pyridine released; the resulting aqueous solution is freeze dried. The resulting solid is washed with acetonitrile and acetone. The product obtained is a white solid and is analyzed to be 81% active via hyamine titration and 13.66% sodium isethionate via HPLC. The product yield is 27% (8.46 g, 0.0175 mole). $^1$H NMR (300 MHz, D$_2$O, TMS) $\delta$4.4–4.55 (2H, m), $\delta$4.25–4.39 (2H, m), $\delta$4.09–4.15 (~2H $\delta$3.52–3.8 (H, m), $\delta$3.45 (2H, m), $\delta$3.2–3.35 (2H, m), $\delta$0.7–1.7 (23–27H, m). Triplets at $\delta$3.13 and $\delta$3.92 are from residual sodium isethionate. Broad singlet at $\delta$4.73 is from residual water. Singlet at $\delta$2.05 is from acetone, IR (nujol); 1746.77 cm$^{-1}$ (carbonyl).

All actives produced in this Example were analyzed for isethionate levels and alcohol levels by HPLC. In addition, they were analyzed for % NaCl, (silver nitrate titration), % Na$_2$SO$_3$, (iodide titration), % Na$_2$SO$_4$, (lead chloride titration) using standard methods. Percent water was determined by NMR.

The results of the preparation of the carbonate, isethionate based actives reported in Table 1 below is as follows:

TABLE 1

| | PREPARATION OF CARBONATE SURFACTANTS | | | |
|---|---|---|---|---|
| Active | Structure | % RXN Yield | % Purity | Appearance |
| SEDC | $CH_3(CH_2)_{11}-O-\overset{O}{\overset{\|}{C}}-O-CH_2-CH_2-SO_3^-Na^+$ | 86 | 99+ | White, crystalline |
| SIDC | $CH_3(CH_2)_{11}-O-\overset{O}{\overset{\|}{C}}-O-CH-CH_2-SO_3^-Na^+$ <br> $\quad\quad\quad\quad\quad\quad\quad\quad\quad\quad\quad\quad\|$ <br> $\quad\quad\quad\quad\quad\quad\quad\quad\quad\quad\quad\quad CH_3$ | 58 | 99+ | White, crystalline |
| S2DBC | $CH_3(CH_2)_{11}-O-\overset{O}{\overset{\|}{C}}-O-CH-CH_2-SO_3^-Na^+$ <br> $\quad\quad\quad\quad\quad\quad\quad\quad\quad\quad\quad\quad\|$ <br> $\quad\quad\quad\quad\quad\quad\quad\quad\quad\quad\quad\quad C_2H_5$ | 65 | 99+ | White, crystalline |
| SE2DC | $CH_3(CH_2)_9-CH-O-\overset{O}{\overset{\|}{C}}-O-CH_2-CH_2-SO_3^-Na^+$ <br> $\quad\quad\quad\quad\quad\quad\|$ <br> $\quad\quad\quad\quad\quad\quad CH_3$ | 57 | 99+ | White, crystalline |
| SI2DC | $CH_3(CH_2)_9-CH-O-\overset{O}{\overset{\|}{C}}-O-CH-CH_2-SO_3^-Na^+$ <br> $\quad\quad\quad\quad\quad\quad\|\quad\quad\quad\quad\quad\quad\|$ <br> $\quad\quad\quad\quad\quad\quad CH_3\quad\quad\quad\quad\quad CH_3$ | 20 | 99 | White, crystalline |
| SEC16GC | $C_8H_{17}-CH-CH_2-O-\overset{O}{\overset{\|}{C}}-O-CH_2-CH_2-SO_3^-Na^+$ <br> $\quad\quad\quad\quad\|$ <br> $\quad\quad\quad [C_6H_{13}]^*$ | 72 | 84.4 | White, tacky solid |
| SEC18GC | $C_{10}H_{23}-CH-CH_2-O-\overset{O}{\overset{\|}{C}}-O-CH_2-CH_2-SO_3^-Na^+$ <br> $\quad\quad\quad\quad\|$ <br> $\quad\quad\quad [C_6H_{13}]^*$ | 70 | 92 | White, tacky solid |

TABLE 1-continued

PREPARATION OF CARBONATE SURFACTANTS

| Active | Structure | % RXN Yield | % Purity | Appearance |
|---|---|---|---|---|
| SED(2EO)C | $CH_3-(CH_2)_{11}-(EO)_2-O-\overset{O}{\underset{\|}{C}}-O-CH_2-CH_2-SO_3^-Na^+$ | 49 | 77 | White, tacky solid |
| SED(4EO)C | $CH_3-(CH_2)_{11}-(EO)_4-O-\overset{O}{\underset{\|}{C}}-O-CH_2-CH_2-SO_3^-Na^+$ | 30 | 77 | White, tacky solid |
| SET/D(2EO)C | $CH_3-(CH_2)_{11-13}-(EO)_2-O-\overset{O}{\underset{\|}{C}}-O-CH_2-CH_2-SO_3^-Na^+$ | 27 | 81 | White, tacky solid |

*Note:
[$C_6H_{13}$] chains are branched.
EO = $-O-CH_2-CH_2$

Various characteristics of carbonated isethionates were compared to an isethionate ester (sodium lauroyl isethionate) SLI and the results are set forth below in Table 2. The Guerbet derivatives were not tested. vide the same surfactancy benefits as a surfactant with higher CMC. As can be seen from the table above, the carbonates have lower CMC values and are, therefore, believed to provide more effective surfactancy.

TABLE 2

TEST RESULTS CARBONATED ISETHIONATES

| Active | CMC (mM) | Krafft Pt. (°C.) | Foam Ht. (mM) Initial Ht. 10 min Ht. | % Zein Solub. | Ca + 2 Needed for Prec. (ppm) | Hydrolytic Stability/Days $t_{\frac{1}{2}}$, pH 9, 40° C. |
|---|---|---|---|---|---|---|
| SLI | 6.2 | 24 | negligible | 55 | 51 | 1.0 |
| SEDC | 2.52 | 24 | 159/149 | 49 | 150 | 2.3 |
| SIDC | 2.39 | 15 | 165/161 | 51 | 2000 | 11.9 |
| S2DBC | 1.46 | 0 | 166/142 | 41 | 725 | 43.0 |
| SE2DC | 3.7–4.0 | 0 | 162/160 | 47 | >2700 | 9.3 |
| S12DC | 2.6–2.8 | 30 | 156/149 | 49 | 2500 | ≈70 |
| SEC 16GC | — | — | 170/159 | — | — | — |
| SEC 18GC | — | — | 44/35 | — | — | — |
| SED (2EO)C | — | — | 165/160 | 25 | — | — |
| SED (4EO)C | — | — | 158/152 | 17 | — | — |
| SET/D (2EO)C | — | — | 159/153 | 25 | — | — |

Each of these characteristics, how they are quantified, and an explanation of the significance of these numbers is set forth in greater detail below.

1. Critical Micelle Concentration (CMC)

The CMC is defined as the concentration of a surfactant at which it begins to form micelles in solution rather than precipitate. Specifically, materials that contain both a hydrophobic group and a hydrophilic group, (such as surfactants), will tend to distort the structure of the solvent (i.e, water) they are in and, therefore, increase the free energy of the system. They therefore, concentrate at the surface, whereby orienting so that their hydrophobic groups are directed away from the solvent, the free energy of the solution is minimized. Another means of minimizing the free energy can be achieved by the aggregation of these surface-active molecules into clusters or micelles with their hydrophobic groups directed toward the interior of the cluster and their hydrophilic groups directed toward the solvent.

The value of the CMC is determined by surface tension measurements using the Wilhemy plate method. While not wishing to be bound by theory, it is believed that a low CMC is a measure of surface activity (i.e, lower CMC of one surfactant versus another indicates the surfactant with lower CMC is more surface active). In this regard, it is believed that lower CMC signifies that lesser amounts of a surfactant are required to provide the same surfactancy benefits as a surfactant with higher CMC. As can be seen from the table above, the carbonates have lower CMC values and are, therefore, believed to provide more effective surfactancy.

2. Krafft Points

The temperature at and above which surfactants begin to form micelles instead of precipitates is referred to as Krafft point (Tk) and at this temperature the solubility of an ionic surfactant becomes equal to its CMC.

Krafft point was measured by preparing a 1% dispersion of the surfactant in water. If the surfactant was soluble at room temperature, the solution was cooled to 0° C. When the surfactant did not precipitate out, its Krafft point was considered to be <0° C. If it precipitated out, the solution was slowly warmed with stirring in a water bath. The temperature at which the precipitate dissolved was determined to be the Krafft point.

If the Krafft point was above room temperature, the solution was first heated rapidly to dissolve all the surfactant. It was then cooled until precipitation occurred, and was then slowly warmed to determine the Krafft point described above.

While not wishing to be bound by theory, it is believed that lower Krafft points are indicative of a surfactant being more soluble in aqueous system. In addition, it is believed that surfactants with lower Krafft points are easier to formulate in multi-electrolyte systems because of their greater tolerance to salt.

From the table above, it can be seen that the SEDC material has the same Krafft point as the SLI and the SI2 DC is higher. However, the balance have much lower Krafft point indicating greater solubility and salt tolerance as discussed above.

3. Foam Height

Foam is an important attribute in many consumer products. Foam is one of the dominant factors that determines the commercial value of products such as shampoo, soap, etc. Also, acceptability of many consumer products is closely related to the quality of texture and the foam they produce.

Since most of the foaming data on surfactants is typically obtained by the Ross-Miles method (Ross, J. and Miles, G.D., Am. Soc. For Testing Material Method D1173-53 Philadelphia, Pa. (1953); Oil & Soap (1958) 62:1260) the foaming ability of these surfactants was also acquired using this method.

In the Ross-Miles method, 200 mL of a solution of surfactant contained in a pipette of specified dimensions with a 2.9 mm-i.d. orifice is allowed to fall 90 cm onto 50 mL of the same solution contained in a cylindrical vessel maintained at a given temperature (often 60° C.) by means of a water jacket. The height of the foam produced in the cylindrical vessel is read immediately after all the solution has run out of the pipette (initial form height) and then again after a given amount of time (generally, 5 min.).

Using this method, the form production (measured initially) and foam stability (the height after 10 minutes) are reported. All of the foaming was achieved at 45° C. in water with 120 ppm calcium hardness. The foam height is represented in millimeters (mm).

As indicated in the table above, foam heights for the noncarbonated isethionate are negligible while heights for the carbonated isethionates are quite high.

4. Zein Test

Assessing Mildness

Many factors have been reported to have an influence on skin irritation such as removal of skin lipids, loss of naturally occurring hygroscopic materials in the stratum corneum, adsorption, protein denaturation, and epidermal lyposomal injury. Although there are many hypotheses regarding skin irritation, it is generally believed that surfactants become irritants because they penetrate the stratum corneum which is a "barrier" and then react with the inner cells of the epidermis.

Traditionally, the study of percutaneous absorption has focused on measuring the diffusion of chemicals (e.g., surfactants through stratum corneum). Diffusion through an organ as complex as skin and its associated adnexal appendages is challenging to measure, model, and reproduce. Another challenge of cutaneous metabolism is to assess the irritating potential, toxicity, and therapeutic potential of the penetrating compounds.

In vivo, the skin metabolism and percutaneous absorption are very difficult to measure. Finding adequate detection methods and setting up proper experiments are not easy tasks. In vitro studies, however, are used because of the simplicity of the experimental conditions.

We have obtained information on mildness potentials of the surfactant by carrying out in vitro tests which have been demonstrated to correlate reasonably well with in vivo tests. These tests, however, are only an approximation and may prove deceptive in analysis in some situations of other types of in vitro tests or indeed in vivo tests may have different results.

In Vitro Zein Solubilization Test

Gotte (E. Gotte, Proc. Int. Cong. Surface Active Subs., 4th Brussels (1964), 3, 83-90) and Schwinger (M. J. Schwinger, Kolloid-Z. Z. Poly., (1969), 233, 989) have shown that a surfactant's ability to solubilize zein, an insoluble maize protein, correlates reasonably well with surfactant irritation potential. Specifically, the lower the amount of zein protein dissolved, usually the milder a surfactant is. Conversely, the more zein dissolved, typically the more irritating the surfactant is. In order to test irritancy potential, a 1% solution of surfactant (30 mls) was added to 1.5 g zein and stirred at room temperature for 1 hr. Residual zein was collected and dried to constant weight. Differences between starting and residual weights were used to calculate % zein dissolved.

In the Table above, the decrease in zein dissolved going from the non carbonate material to the carbonate material indicates a decrease in irritation potential. A cautionary note must be observed, however, in that other types of in vitro tests may give different or even opposite results.

5. Calcium sensitivity

The calcium ion stability of carbonated isethionates was measured by a modified Hart method (Witkes, et al. *J. Ind. Eng. Chem.*, 29, 1234–1239 (1937)). The surfactant solution was titrated with a calcium ion solution. The endpoint was determined by visual observation of the cloudiness of the surfactant solution.

Many surfactants such as fatty soap are known to chelate to calcium ion to form calcium salts which are usually insoluble in aqueous media. This will lead to the loss of their surfactant properties. Calcium "insensitive" surfactants have unique advantageous properties for many applications such as a formulation for a liquid cleanser. In the case of the carbonated isethionates, it was noticed that a large amount of calcium ion was added before precipitation was seen. For most of these isethionates, the precipitation limit was not reached even at levels well over an order of magnitude higher than the precipitation limit for the non-carbonated isethionate.

As clearly seen from the table above, carbonated, isethionates are much less sensitive to calcium than the non-carbonate compound.

6. Hydrolytic Stability

These actives were evaluated for their hydrolytic stability at pH 9, 40° C. The carbonates appear to be more hydrolytically stable at basic pH than the corresponding ester surfactants. It is theorized that as the amount of branching is increased, the stability increases.

The $t_{\frac{1}{2}}$ (half life) for these actives their decrease in concentration with time in a buffered solution using reverse phase HPLC. The actives were monitored at concentrations below their CMC using a reverse phase column and conductivity detection which allows for low level detection. By plotting the ln concentration (or ln area) with time, a straight line was noted indicative of pseudo first order kinetics. The surfactants were prepared at $5 \times 10^{-4}$M in pH 9.0 buffer (NaHCO$_3$) with 5% CH$_3$CN and maintained in a water bath at 40° C. A 200 μl injection of each solution was made at various time intervals.

| Column: | Wescan Surfactant Column - Reverse Phase; 25 cm |
|---|---|
| Mobile Phase: | 0.1% Ammonium Acetate in 45:55 DLN NeO |
| Flowrate: | 1.3 ml/minute |
| Detector: | Conductivity (baseline conductivity 1030 S); Gain: 0.005; Range: 1000 |
| Pressure: | 2000 psi |
| Retention Times: | SEDC - 5.3 minutes |
| | SIDC - 6.9 minutes |
| | S2DBC - 8.0 minutes |
| | SE2DC - 6.1 minutes |
| | SI2DC - 6.2 minutes |

(Note: Retention times will vary depending on the conductivity of the mobile phase.)

In Summary—Table 2 Results show:

(1) Novel carbonate surfactants based onisethionate are easily prepared in a two step procedure from fatty alcohols. The parent molecule SEDC is prepared in 86% yield. Most actives were purified to >99% active.

(2) The carbonate surfactants exhibit greater hydrolytic stability over their ester counterparts at pH 9. The stability increases with branching.

(3) The carbonate surfactants exhibit CMCs below that for sodium lauroyl isethionate (SLI).

(4) The carbonate surfactants show good foam performance in 120 ppm hard water unlike their ester counterparts.

(5) The branched carbonate actives show greater solubility in the presence of calcium chloride. The parent SEDC shows a greater calcium insensitivity than the ester SLI.

EXAMPLE 2

Two toilet bar compositions containing fatty acid esters of carbonated isethionic acid and one toilet bar composition with a non-carbonated counterpart are prepared and the compositions are set forth below:

| Components (% by Wt.) | Composition 1 | Composition 2 | Composition 3 |
|---|---|---|---|
| Sodium cocoyl isethionate | — | 24.89 | 49.78 |
| SEDC | 51.37 | 25.69 | — |
| Lauric acid | 21.6 | 10.8 | — |
| Stearic acid | — | 10.08 | 20.15 |
| Coconut fatty acid | — | 1.54 | 3.01 |
| Soap (Mixture of tallow and coconut) | 8.02 | 8.02 | 8.02 |
| Sodium stearate | 3.01 | 3.01 | 3.01 |
| Sodium alkyl benzene sulfonate | 2.01 | 2.01 | 2.01 |
| Sodium chloride | 8.34 | 4.3 | 0.35 |
| Sodium isethionate | — | 2.34 | 4.68 |
| Water | 5.01 | 5.21 | 5.21 |
| Miscellaneous | 0.64 | 2.11 | 3.78 |

EXAMPLE 3 -

Light Duty Liquid Containing Carbonated Isethionates

A composition containing the following ingredients may be prepared.

| Component | % By Weight |
|---|---|
| Ammonium alkyl benzene sulfonate | 19.0 |
| SIDC | 11.0 |
| Lauric/myristic monoethanolamide | 3.0 |
| Sodium xylene sulfonate | 5.0 |

-continued

| Component | % By Weight |
|---|---|
| Preservative, fragrance, dye and water | to 100% |

EXAMPLE 4

Facial Cleanser Containing Carbonated Isethionates

A composition containing the following ingredients may be prepared.

| Component | % By Weight |
|---|---|
| SEDC | 13.0 |
| Coco amido propyl betaine | 4.5 |
| Carbopol 940* | 1.0 |
| Laponite | 0.05 |
| Lauric/myristic acid | 5.6 |
| Sodium chloride | 2.8 |
| Preservative, fragrance and water | to 100% |

It is understood that the examples and embodiments described herein are for illustrative purposes only and that various modifications or changes in the light thereof will be suggested to persons skilled in the art and are to be included within the spirit and purview of this application and the scope of the appended claims.

What is claimed is:

1. A compound of the formula:

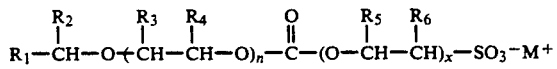

wherein n is a number from 0 to 10;

wherein x is 1 or 2;

wherein $R_1$ through $R_6$ inclusive may be independently hydrogen, aryl, cycloalkyl, alkylaryl, alkylene or straight or branched $C_{1-18}$ alkyl wherein the total number of carbon atoms in all R groups taken together is not greater than 20; and wherein $M^+$ is alkali metal, alkaline earth metal, ammonium or alkylammonium.

2. A compound as defined in claim 1 wherein n is an integer from 0 to 4.

3. A compound as defined in claim 1 wherein n is 0; x is 1; $R_1$, $R_2$, $R_5$ and $R_6$ are as defined and $M^+$ is $Na^+$.

4. A compound wherein R may vary and may be a mixture of $C_{1-18}$ and wherein n and x may vary independently.

5. A composition comprising:

(1) 2-85% by weight of a surfactant selected from the group consisting of anionic, nonionic, cationic, ampholytic and zwitterionic surfactants or mixtures thereof; and (2) A compound of the formula:

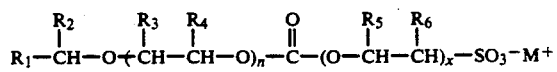

wherein n is a number from 0 to 10;

wherein x is 1 or 2;

wherein $R_1$ through $R_6$ inclusive may be independently hydrogen, aryl, cycloalkyl, alkylaryl, alkylene or straight or branched $C_{1-18}$ alkyl wherein the total number of carbon atoms in all R groups taken together is not greater than 20; and wherein $M^+$ is alkali metal, alkaline earth metal, ammonium or alkylammonium.

6. A composition according to claim 5 wherein n is 0 to 4.

7. A composition according to claim 5 wherein n is 0; x is 1; $R_1$, $R_2$, $R_5$ and $R_6$ are as defined and $M^+$ is $Na^+$.

8. A composition according to claim 5 wherein $R_1$ through $R_6$ may vary independently and may be a mixture of $C_{1-18}$ and wherein n and x may vary independently.

9. A composition according to claim 5, wherein the composition is a toilet bar composition.

10. A composition according to claim 5, wherein the composition is a hand dishwashing composition.

11. A composition according to claim 5, wherein the composition is a facial cleanser composition.

12. A compound as defined in claim 1 wherein:
n is a number selected from 0, 1 and 2;
x is 1 or 2,
$R_1$ is $-C_{10}H_{21}$,
$R_2$ is $-CH_3$,
$R_3$ is H,
$R_4$ is H,
$R_5$ is H,
$R_6$ is H, and
$M^+$ is $Na^+$ 13. A composition comprising:
(1) 2-85% by weight of a surfactant selected from the group consisting of anionic, nonionic, cationic, ampholytic and zwitterionic surfactants or mixtures thereof; and
(2) A compound of the formula:

$$R_1-\overset{R_2}{\underset{|}{CH}}-O+\overset{R_3}{\underset{|}{CH}}-\overset{R_4}{\underset{|}{CH}}-O)_n-\overset{O}{\overset{\|}{C}}-(O-\overset{R_5}{\underset{|}{CH}}-\overset{R_6}{\underset{|}{CH}})_x-SO_3^-M^+$$

n is a number selected from 0, 1 and 2;
x is 1 or 2,
$R_1$ is $-C_{10}H_{21}$,
$R_2$ is $-Ch_3$,
$R_3$ is H,
$R_4$ is H,
$R_5$ is H,
$R_6$ is H, and
$M^+$ is $Na^+$

* * * * *